(12) United States Patent
Goldstein et al.

(10) Patent No.: US 7,879,488 B2
(45) Date of Patent: Feb. 1, 2011

(54) APPARATUS AND METHOD FOR A POWER SOURCE CASING WITH A STEPPED BEVELLED EDGE

(75) Inventors: Leonard I. Goldstein, Shoreview, MN (US); Peter J. Lamb, Minneapolis, MN (US); Jason A. Shiroff, Minneapolis, MN (US); Eric Stemen, Roseville, MN (US); Steven E. Schultz, West Lakeland, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1192 days.

(21) Appl. No.: 11/467,801

(22) Filed: Aug. 28, 2006

(65) Prior Publication Data

US 2008/0050649 A1    Feb. 28, 2008

(51) Int. Cl.
| H01M 2/00 | (2006.01) |
| H01M 2/02 | (2006.01) |
| H01M 2/04 | (2006.01) |
| H01M 2/08 | (2006.01) |
| F16J 9/12 | (2006.01) |

(52) U.S. Cl. .................. 429/176; 429/163; 429/175; 429/178; 429/179; 277/460

(58) Field of Classification Search ............ 277/460
See application file for complete search history.

(56) References Cited

U.S. PATENT DOCUMENTS

| 3,993,508 A | 11/1976 | Erlichman |
| 4,113,921 A | 9/1978 | Goldstein et al. |
| 4,169,003 A | 9/1979 | Dangel et al. |
| 4,205,364 A | 5/1980 | Pereira, Jr. |
| 4,232,099 A | 11/1980 | Sullivan |
| 4,243,042 A | 1/1981 | Ware |
| 4,425,412 A | 1/1984 | Dittmann et al. |
| 4,659,636 A | 4/1987 | Suzuki et al. |
| 4,745,039 A | 5/1988 | Yoshinaka |
| 5,131,388 A | 7/1992 | Pless et al. |

(Continued)

FOREIGN PATENT DOCUMENTS

WO    WO-02/43090 A2    5/2002

OTHER PUBLICATIONS

Harper, Modern Plastics Handbook, p. 9.35-9.70, 2000.*

*Primary Examiner*—Dah-Wei D Yuan
*Assistant Examiner*—Steven Scully
(74) *Attorney, Agent, or Firm*—Schwegman, Lundberg & Woessner, P.A.

(57) ABSTRACT

One embodiment of the present subject matter includes a stack of substantially planar electrodes, the stack in alignment and having a stack form factor. Embodiments include a first housing portion including a first beveled edge at least partially defining a first stack aperture adapted to at least partially receive the stack, the first stack opening having a first thickness proximal the beveled edge, and a second thickness away from the first beveled edge and a second housing portion including a second edge defining a second stack aperture adapted to at least partially receive the stack. Embodiments are included wherein the second housing portion is joined to the first housing portion such that the first housing portion and the second housing portion define an interior space which substantially conforms to the stack form factor.

20 Claims, 3 Drawing Sheets

U.S. PATENT DOCUMENTS

| | | | |
|---|---|---|---|
| 5,173,375 A | 12/1992 | Cretzmeyer et al. | |
| 5,175,067 A | 12/1992 | Taylor et al. | |
| 5,306,581 A | 4/1994 | Taylor et al. | |
| 5,422,200 A | 6/1995 | Hope et al. | |
| 5,434,017 A | 7/1995 | Berkowitz et al. | |
| 5,503,948 A | 4/1996 | MacKay et al. | |
| 5,691,079 A | 11/1997 | Daugaard | |
| 5,774,261 A | 6/1998 | Omori et al. | |
| 5,776,632 A | 7/1998 | Honegger | |
| 5,811,206 A | 9/1998 | Sunderland et al. | |
| 5,876,424 A | 3/1999 | O'Phelan et al. | |
| 5,882,362 A | 3/1999 | Muffoletto et al. | |
| 5,926,362 A | 7/1999 | Muffoletto et al. | |
| 6,004,692 A | 12/1999 | Muffoletto et al. | |
| 6,010,803 A | 1/2000 | Heller, Jr. et al. | |
| 6,139,986 A | 10/2000 | Kurokawa et al. | |
| 6,162,264 A | 12/2000 | Miyazaki et al. | |
| 6,225,778 B1 | 5/2001 | Hayama et al. | |
| 6,330,925 B1 | 12/2001 | Ovshinsky et al. | |
| 6,334,879 B1 * | 1/2002 | Muffoletto et al. | 29/25.03 |
| 6,430,031 B1 | 8/2002 | Dispennette et al. | |
| 6,459,566 B1 | 10/2002 | Casby et al. | |
| 6,498,951 B1 | 12/2002 | Larson et al. | |
| 6,522,525 B1 | 2/2003 | O'Phelan et al. | |
| 6,602,742 B2 | 8/2003 | Maletin et al. | |
| 6,610,443 B2 | 8/2003 | Paulot et al. | |
| 6,613,474 B2 | 9/2003 | Frustaci et al. | |
| 6,801,424 B1 | 10/2004 | Nielsen et al. | |
| 6,807,048 B1 | 10/2004 | Nielsen et al. | |
| 6,819,544 B1 | 11/2004 | Nielsen et al. | |
| 6,833,987 B1 | 12/2004 | O'Phelan | |
| 6,836,683 B2 | 12/2004 | Nielsen et al. | |
| 6,842,328 B2 | 1/2005 | Schott et al. | |
| 6,859,353 B2 | 2/2005 | Elliott et al. | |
| 6,881,516 B2 | 4/2005 | Aamodt et al. | |
| 6,922,330 B2 | 7/2005 | Nielsen et al. | |
| 6,963,482 B2 | 11/2005 | Breyen et al. | |
| 2003/0017372 A1 | 1/2003 | Probst et al. | |
| 2003/0077509 A1 | 4/2003 | Probst et al. | |
| 2003/0165744 A1 | 9/2003 | Schubert et al. | |
| 2004/0018425 A1 | 1/2004 | Kejha et al. | |
| 2004/0062986 A1 * | 4/2004 | Aamodt et al. | 429/181 |
| 2004/0114311 A1 | 6/2004 | O'Phelan et al. | |
| 2004/0127952 A1 | 7/2004 | O'Phelan et al. | |
| 2004/0147960 A1 | 7/2004 | O'Phelan et al. | |
| 2004/0147961 A1 | 7/2004 | O'Phelan et al. | |
| 2004/0174658 A1 | 9/2004 | O'Phelan et al. | |
| 2004/0193221 A1 | 9/2004 | O'Phelan et al. | |
| 2004/0215281 A1 | 10/2004 | O'Phelan et al. | |
| 2004/0240153 A1 | 12/2004 | Nielsen et al. | |
| 2004/0258988 A1 | 12/2004 | Nielsen et al. | |
| 2004/0260354 A1 | 12/2004 | Nielsen et al. | |
| 2005/0002147 A1 | 1/2005 | Nielsen et al. | |
| 2005/0010253 A1 | 1/2005 | O'Phelan et al. | |
| 2005/0017888 A1 | 1/2005 | Sherwood et al. | |
| 2005/0052825 A1 | 3/2005 | O'Phelan | |
| 2005/0112460 A1 | 5/2005 | Howard et al. | |
| 2005/0162810 A1 | 7/2005 | Seitz et al. | |
| 2005/0190530 A1 | 9/2005 | Muffoletto et al. | |
| 2005/0221171 A1 | 10/2005 | Haasl et al. | |

* cited by examiner

APPARATUS AND METHOD FOR A POWER SOURCE CASING WITH A STEPPED BEVELED EDGE

TECHNICAL FIELD

This disclosure relates generally to at least partially sealed containers, and more particularly to system and method for a power source casing with a stepped beveled edge.

BACKGROUND

Containers often are comprised of multiple parts which are assembled. Power sources, such as batteries and capacitors, often include subcomponents which are disposed in a container. Self-powered implantable devices can use a power source having such a container. It is urged that implantable devices have a form factor of a reduced size. This is due, in part, to the preference of care providers to implant smaller devices. This is additionally due to the comfort preference of end-user patients.

One problem with reducing size of implantable devices is packaging power sources. Smaller power sources are desired. Smaller power sources should satisfy an ongoing need for containers which are compatible with a range of manufacturing tools. This need encompasses the need for allowing container construction methods which join container parts using heat. For example, improved designs should allow for laser welding. Smaller sizes emphasize an ongoing need for insulation from heat flow with respect to heat sensitive subcomponents. Power sources of a reduced size should also satisfy an ongoing need to provide designs which enable precise assembly. Among the benefits of precise assembly is an improvement in manufacturing yield.

SUMMARY

The above-mentioned problems and others not expressly discussed herein are addressed by the present subject matter and will be understood by reading and studying this specification.

One embodiment of the present subject matter includes a stack of substantially planar electrodes, the stack in alignment and having a stack form factor. The embodiment additionally includes a first planar housing portion including a first beveled edge at least partially defining a first stack aperture adapted to at least partially receive the stack, the first stack opening having a first thickness proximal the beveled edge, and a second thickness away from the first beveled edge. The embodiment also includes a second planar housing portion including a second edge defining a second stack aperture adapted to at least partially receive the stack. In the embodiment, the second planar housing portion is joined to the first planar housing portion such that they are substantially coplanar and the first planar housing portion and the second planar housing portion define an interior space which substantially conforms to the stack form factor.

An additional embodiment of the present subject matter includes stacking into a stack a plurality of substantially planar electrodes, the stack including the plurality of substantially planar electrodes in alignment. The embodiment includes pressing a first beveled edge of a first cup shaped housing against a second beveled edge of a second cup shaped housing such that the first housing portion and the second housing portion encapsulate the stack. The embodiment further includes joining the first beveled edge of the first housing portion to the edge of the second housing portion. In the embodiment, the first beveled edge of the first housing portion encourages substantially coextensive alignment of the first beveled edge with the edge of the second housing portion.

Also, one embodiment of the present subject matter includes a stack of substantially planar electrodes. The embodiment includes a first housing including a first edge, the first edge being shaped for passage of the stack. The embodiment includes a second housing including a second edge defining an opening shaped for passage of the stack. The embodiment also includes means for encouraging self-alignment of the first edge and the second edge into a coextensive alignment when the first edge is pressed to the second edge such that the first housing and the second housing encapsulate the stack.

The present subject matter contemplates embodiments having various features. One feature present in some embodiment is that the electrodes comprise a battery. In other embodiments, the electrodes comprise a capacitor. In some embodiments, the electrodes provide energy in a pacemaker. In some embodiments, the electrodes provide energy in a defibrillator. In some embodiments, the second planar housing portion includes a second substantially planar face with a second wall extending away from the substantially planar housing portion. In some embodiments, the first planar housing portion includes a substantially planar face with a wall extending away from the substantially planar housing portion. In some embodiments, the edge of the second housing portion includes a second beveled edge which encourages substantially coextensive alignment with the first beveled edge of the first housing portion. Seals are used in some embodiments.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

DETAILED DESCRIPTION

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

Various embodiments of the present subject matter concern housings. Housings of the present subject matter includes housings having a first portion and a second portion which are assembled to house components. Some embodiments of the present subject matter join two or more housing portions together so that they are joined in use. Various embodiments of the present subject matter provide housings which includes features which encourage alignment of the housing portions as they are assembled.

Among the components housed in the housings of the present subject matter are power sources, in various embodiments. Some embodiments use power sources which are disposed in implantable medical devices. As such, the implantable medical devices are at least partially self powered. Among the power source embodiments of the present subject matter are batteries and capacitors. Capacitors, in various embodiments, include electrodes. In some embodiments, the electrodes are layered together. In some embodiments, the electrodes are stacked into a stack. The present subject matter includes stacks which include a plurality of substantially planar electrodes. Some embodiments include two layers, namely an anode and a cathode. Additional embodiments include a stack of substantially planar electrodes in which multiple layers form and anode. Stacks in which multiple layers form a cathode are contemplated by the present subject matter.

Batteries including at least two electrodes are contemplated by the present subject matter. In some embodiments, the electrodes are layered together. In some embodiments, the electrodes are stacked into a stack. The present subject matter includes stacks which include a plurality of substantially planar electrodes. Some embodiments include two layers, namely an anode and a cathode. Additional embodiments include a stack of substantially planar electrodes in which multiple layers form and anode. Stacks in which multiple layers form a cathode are contemplated by the present subject matter.

Figure 1:
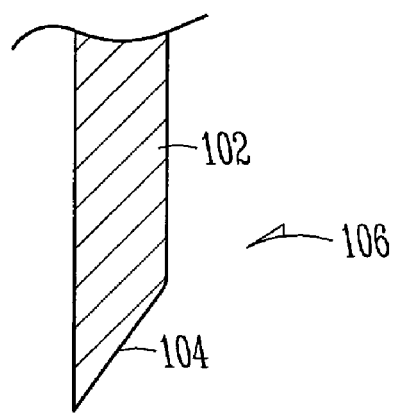
FIG. 1 illustrates a cross section of a beveled edge of a portion of a housing, according to one embodiment of the present subject matter.

FIG. 1 illustrates a cross section of a beveled edge of a portion of a housing, according to one embodiment of the present subject matter. Various embodiments of the present subject matter include a housing portion 102. The housing portion is formed according to one of the various processes contemplated by embodiments within the present subject matter, including, but not limited to, drawing, molding, milling, punching, stamping, or other processes not expressly recited herein.

Various embodiments of the present subject matter include an edge 104. Embodiments of the present subject matter join edge 104 to another housing portion. Various joining operations are contemplated by the present subject matter, including, but not limited to, welding, adhesive, interference fitting, snap fitting, and high energy density processes such as electron beam welding, laser welding. Other joining processes which are not expressly recited herein are additionally contemplated. In various embodiments, the edge defines an opening to an interior 106 of the housing portion.

In various embodiments, a bevel is depicted opening the interior in the illustration. Embodiments are contemplated in which the bevel opens to an exterior are additionally contemplated. Additionally, embodiments are contemplated in which edge 104 is not beveled. Embodiments are contemplated in which edge 104 includes a bevel in addition to another feature. Features which may be combined with a bevel include, but are not limited to, steps which run along the face of the bevel, troughs which run along the bevel, and other features not expressly recited herein.

In some embodiments, the edge 102 is an extension of a wall of a cup shaped housing portion. In some embodiments, the edge 102 is an extension of substantially planar housing portion. Housing portion embodiments of the present subject matter include, but are not limited to, these shapes, as well as disk shapes, dish shapes, squared shapes, trapezoidal shapes, nonregular shapes, and additional shapes not expressly recited herein.

Figure 2:
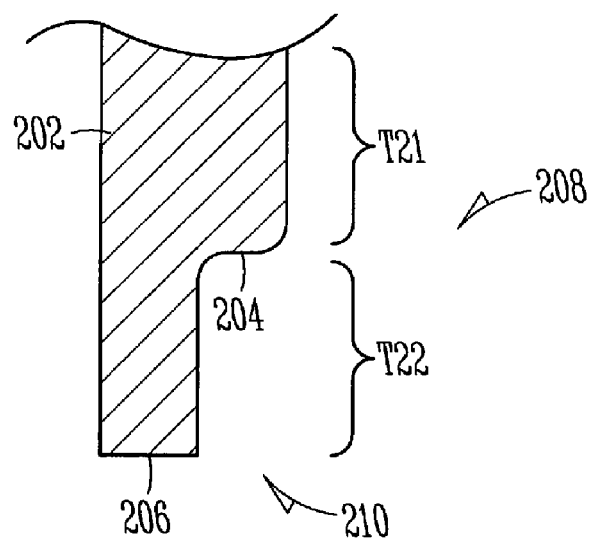
FIG. 2 illustrates a cross section of a step of a portion of a housing, according to one embodiment of the present subject matter.

FIG. 2 illustrates a cross section of a step of a portion of a housing, according to one embodiment of the present subject matter. Various embodiments of the present subject matter include a housing portion 202. The housing portion is formed according to one of the various processes contemplated by embodiments within the present subject matter, including, but not limited to, drawing, molding, milling, punching, stamping, or other processes not expressly recited herein.

Various embodiments of the present subject matter include an edge 206. Embodiments of the present subject matter join edge 206 to another housing portion. Various joining operations are contemplated by the present subject matter, including, but not limited to, welding, adhesive, interference fitting, snap fitting, and high energy density processes such as electron beam welding, laser welding. Other joining processes which are not expressly recited herein are additionally contemplated. In various embodiments, the edge defines an opening to an interior 208 of the housing portion.

Various embodiments include a step 204. Step 204 is a transition between thickness $T_{21}$ and thickness $T_{22}$. It should be noted that while a step shaped transition is realized, other shapes are contemplated including, but not limited to, ramps, curves, nonlinear shapes, and other shapes not expressly recited herein. In various embodiments, a component is disposed in interior 208. In various embodiments, the thickness T21 results in a shorter distance for heat to flow between the housing 202 and the component. As such, heat from housing 202 is more easily flowed to a component in interior 208 along thickness T21, while heat is flowed less efficiently along thickness T22. In some embodiments, a component in interior 208 is disposed in the interior 208 which is sensitive to heat flow. In some of these embodiments, it is beneficial to minimize heat flow from a housing portion 202 the component housed. The step, and the associated recess 210 provide for reduced heat flow to the housed component. In various embodiments, the thickness of the housing portion 202 along portion $T_{22}$ is approximately 0.007 inches, but other thicknesses are contemplated by the present subject matter. Various embodiments of the present subject matter providing a housing portion 202 which is between approximately 0.008 inches thick to approximately 0.016 inches. Some embodiments provide a housing portion 202 which is approximately 0.012 inches thick along portion $T_{21}$. These thicknesses are selected for some embodiments. Embodiments having additionally thicknesses are also contemplated by the present subject matter.

In various embodiments, the edge 206 is an extension of a wall of a cup shaped housing portion. In some embodiments, the edge 206 is an extension of substantially planar housing portion. Housing portion embodiments of the present subject matter include shapes, but are not limited to these shapes.

Figure 3:
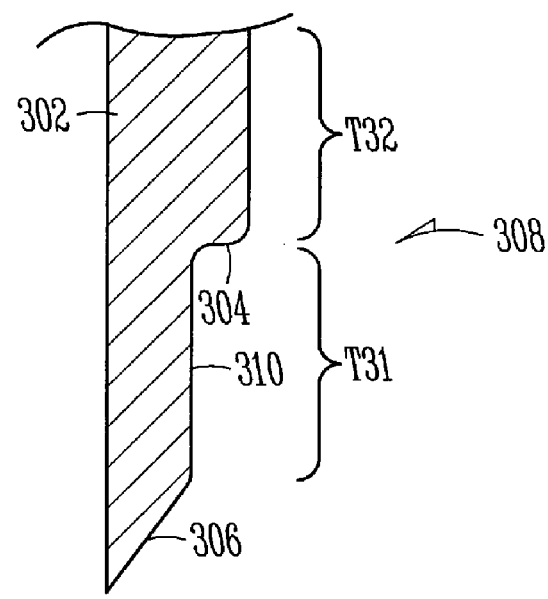
FIG. 3 illustrates a cross section of a portion of a housing including a bevel and a step, according to one embodiment of the present subject matter.

FIG. 3 illustrates a cross section of a portion of a housing including a bevel and a step, according to one embodiment of the present subject matter. The housing portion 302 includes a step 304 and a beveled edge 306. In various embodiments, the step 304 is a transition defined by material extending between thickness $T_{32}$ and thickness $T_{31}$. The illustrated configuration is but one of the configurations contemplated by the present subject matter. For example, transitions between thickness $T_{32}$ and thickness $T_{31}$ may include other shapes. Further, edge 306 can include other features, in various embodiments. In some embodiments, edge 306 is not beveled.

The illustration shows an embodiment in which a first thickness $T_{31}$ exists proximal a beveled edge 306, while a second thickness $T_{32}$ exists away from the beveled edge. Such a configuration provides a recess 310. The recess 310 faces interior space 308. The length of the recess is different in various embodiments. Additionally, the depth of the recess changes in various embodiments.

Figure 4:
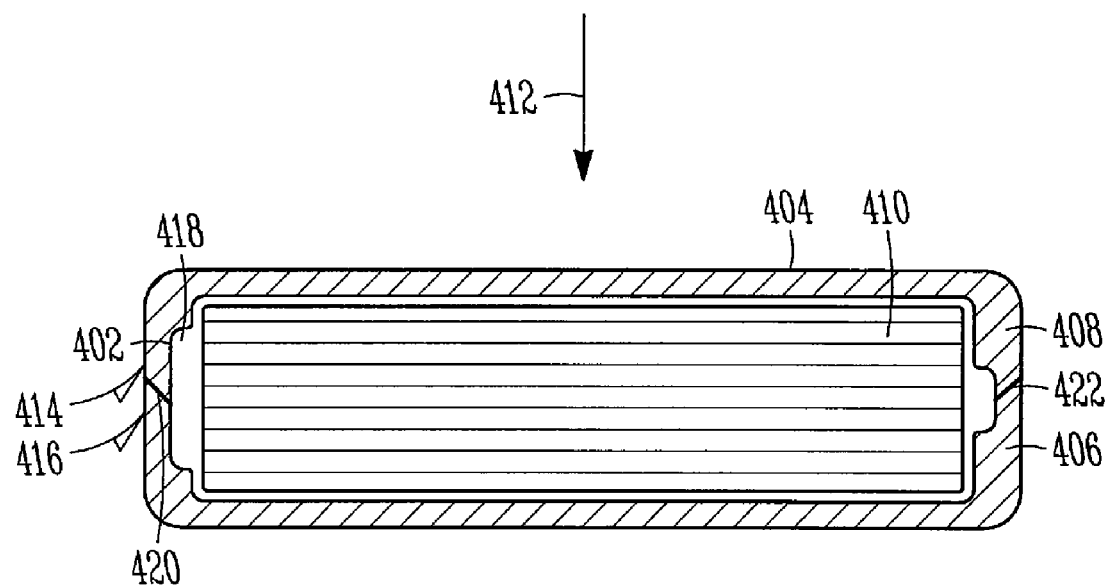
FIG. 4 illustrates a partial cross section of a power source including two mated housing portions, according to one embodiment of the present subject matter.

FIG. 4 illustrates a partial cross section of a power source including two mated housing portions, according to one embodiment of the present subject matter. The illustrated configuration includes a stack 410. In various embodiments, the stack 410 includes a plurality of layers. In some examples, the stack 410 includes a plurality of anode layers which are interconnected to one another. Various embodiments include a plurality of cathode layers which are interconnected to one another.

In various embodiments, the stack is in alignment. Some embodiments put the stack into alignment using visual position recognition. Some embodiments stack the layers into a receptacle. Some of these embodiments stack the layers into a second housing portion 406. Some embodiments place an assembled stack into a housing 406.

The stack 410, in various embodiments, is a capacitor stack. In additional embodiments, the stack is a battery stack. Some embodiments include a feedthrough connected at least one electrode of the stack to a terminal which extends through the first housing portion 404 and/or the second housing portion 406 in isolation from the first housing portion 404 and/or the second housing portion 406. In various embodiments, the feedthrough is sealed. Embodiments are included in which the feedthrough is sealed with an epoxy. Some of these embodiments include an epoxy which permits the escape of gasses disposed in the interior space defined by the first housing portion 404 and the second housing portion 406. Some embodiments include two feedthroughs. In some of these embodiments, the first feedthrough connects a first plurality of electrodes to a terminal which extends through the first housing portion 404 and/or the second housing portion 406 in electrical isolation. In some embodiments, a second feedthrough connects a second plurality of electrodes to a terminal which extends through the first housing portion and/or the second housing portion 406.

First housing portion 404 and second housing portion 406 are mated together, in various embodiments. In some embodiments, they are connected to one another mechanically. The present subject matter contemplates multiple types of mechanical interface embodiments, including, but not limited to, interference fits, clearance fits, snap fits, and other fits not expressly recited herein.

In various embodiments, the first housing portion 404 is jointed to the second housing portion 406. In some of these embodiments, the first housing portion 404 is adhered to the second housing portion 406. Embodiments within the present scope, include, but are not limited to, resins such as epoxy. Various additional joining operations are contemplated by the present subject matter, including, but not limited to, welding, additional adhesives, interference fitting, snap fitting, and high energy density processes such as electron beam welding, laser welding. Other joining processes which are not expressly recited herein are additionally contemplated.

In various embodiments of the present subject matter, an electrode of the stack 410 is connected to the first housing portion 404 and/or the second housing portion 406. Some of these embodiments include a conductor which connects the stack 410 to the first housing portion 404 and/or the second housing portion 406.

Various embodiments of the present subject matter include one or more features which encourage alignment of the first housing portion 404 to the second housing portion 406. In various embodiments, the first housing portion includes first edge portion 414. In various embodiments, the first edge portion defines an opening of the first housing portion 404. In various embodiments, the opening is shaped for passage of the stack 412. In embodiments in which the first housing portion is cup shaped, a stack is positioned at least part of the way through an opening, and is retained in the cup. Additional embodiments include a first housing portion which is not cup shapes. Shapes contemplated by the present subject matter include, but are not limited to, cup shapes, disk shapes, dish shapes, squared shapes, trapezoidal shapes, nonregular shapes, and additional shapes not expressly recited herein.

In various embodiments, a first edge portion 414 and a second edge portion 416 are put into contact with one another during assembly. Various embodiments work to put the first edge portion 414 into mated engagement with the second edge portion 416 of the second housing portion 406. Pressing 412 on the first edge portion 414, has the effect of encouraging alignment of the first edge portion 414 with the second edge portion 416, in various embodiments. As such, features of one or both of the first edge portion 414 and the second edge portion 416 help the first housing portion 404 self-align with the second housing portion 406. In various embodiments, alignment of the first edge portion 414 and the second edge portion 416 means ensure that a first opening defined by the first edge portion 414 is substantially coextensive with a second opening defined by the second edge portion 416.

Such alignment characteristics provide for improved alignment between the first housing portion 404 and the second housing portion 406. An improperly aligned housing, including two or more housing portions, can be a cause for leakage of contents packaged in the housing. Further, misalignment can allow laser light to enter into a housing, in embodiments using lasers to joint a first housing portion and a second housing portion. Such laser light can damage other components. The present subject matter reduces instances of laser light leakage into the interior of the housing. An additional benefit is improving yield in the factory, as fewer housings are assembled out of alignment. A further benefit is that assembly is made simpler, as an assembler only need hold one housing portion against another to provide for alignment. These are just a few of the benefits provided for by the present subject matter.

In some embodiments, the first housing portion 404 and the second housing portion 406 encapsulate stack 410. In various embodiments, the stack 410 has a form factor. Form factors which are contemplated by the present subject matter include, but are not limited to, ovoid, circular, rectangular, trapezoidal, irregular shapes, and additional shapes not listed expressly herein. In various embodiments, the first housing portion 404 and the second housing portion 406 conform to the stack 410. In some embodiments, the first housing portion 404 and the second housing portion 406 substantially form-fit the stack.

Such a relationship between the first housing portion 404, the second housing portion 406, and the stack 410 encourages a reduction in the number of empty spaces in the interior defined by the first housing portion 404 and the second housing portion 406. Such a reduction in space can reduce in the size of the power source component. Smaller power source components can result in smaller implantable devices. Smaller implantable devices reduce difficulty in implantation. Smaller implantable devices additionally improve patient comfort. Smaller power sources can also provide additional room in an implantable device for other components. Theses are just a few of the benefits provided for by the present subject matter.

The present subject matter additionally provides a first thickness 402 proximal a first edge portion 414 and a second thickness 408 extending away from the first edge portion 414. Embodiments of the present subject matter include such a thickness variation along a second housing portion as well. The illustrated configuration provides for a recess 418 which causes a space between the first housing portion 404, the second housing portion 406, and the stack 410. Although the recess pictured is split across a seam 420, the present subject matter is not so limited. Additional embodiments include a recess 418 which is exclusive to a single housing portion.

The thickness of the housing portions 404, 406 varies depending on application. Additionally, the depth of the recess 418 is varied depending on application. In various embodiments, the recess 418 provides for insulation between housing portions 404, 406 and stack 410. In various embodiments, the recess provides insulation between the seam 416 and the stack 410. In some embodiments, the first housing portion 404 and the second housing portion 406 are joined using a heat flow process. Some embodiments use laser welding to join the first housing portion 404 and the second housing portion 406. In some of these embodiments, a heat is produced along the joining seam which is undesirable. In embodiments which package heat sensitive materials in the first housing portion 404 and the second housing portion 406, including embodiments which package a stack 410 in those components, it is desirable to reduce the heat transfer to the packaged components. The present subject matter reduces heat transfer by providing space, in various embodiments. The present subject matter additionally reduces heat by providing an insulative pocket of gas. In various embodiments, the gas in air. A further benefit of the present subject matter is that the beveled nature at seam 418 can reduce instances of laser light reaching packaged components. As discussed above, the beveled nature of at least one housing portion can provide for better alignment in assembly, which can reduce instances of gaps, which can allow laser light to reach packaged components.

Various embodiments are included in the present subject matter in which a first edge portion 414 is planar. Embodiments are included in which a second edge portion 416 is planar. In various embodiments, the first edge portion 414 and the second edge portion 416 are substantially coplanar. In various embodiments, the first edge portion 414 and the second edge portion 416 intersect such that they define a substantially smooth exterior profile 422. Embodiments are contemplated in which the exterior profile is smooth 422, and in which the first edge portion 414 and the second edge portion 416 are not coplanar. Some of these embodiments demonstrate an ovoid shape defined by an assembled first housing portion 404 and second housing portion 406.

Figure 5:
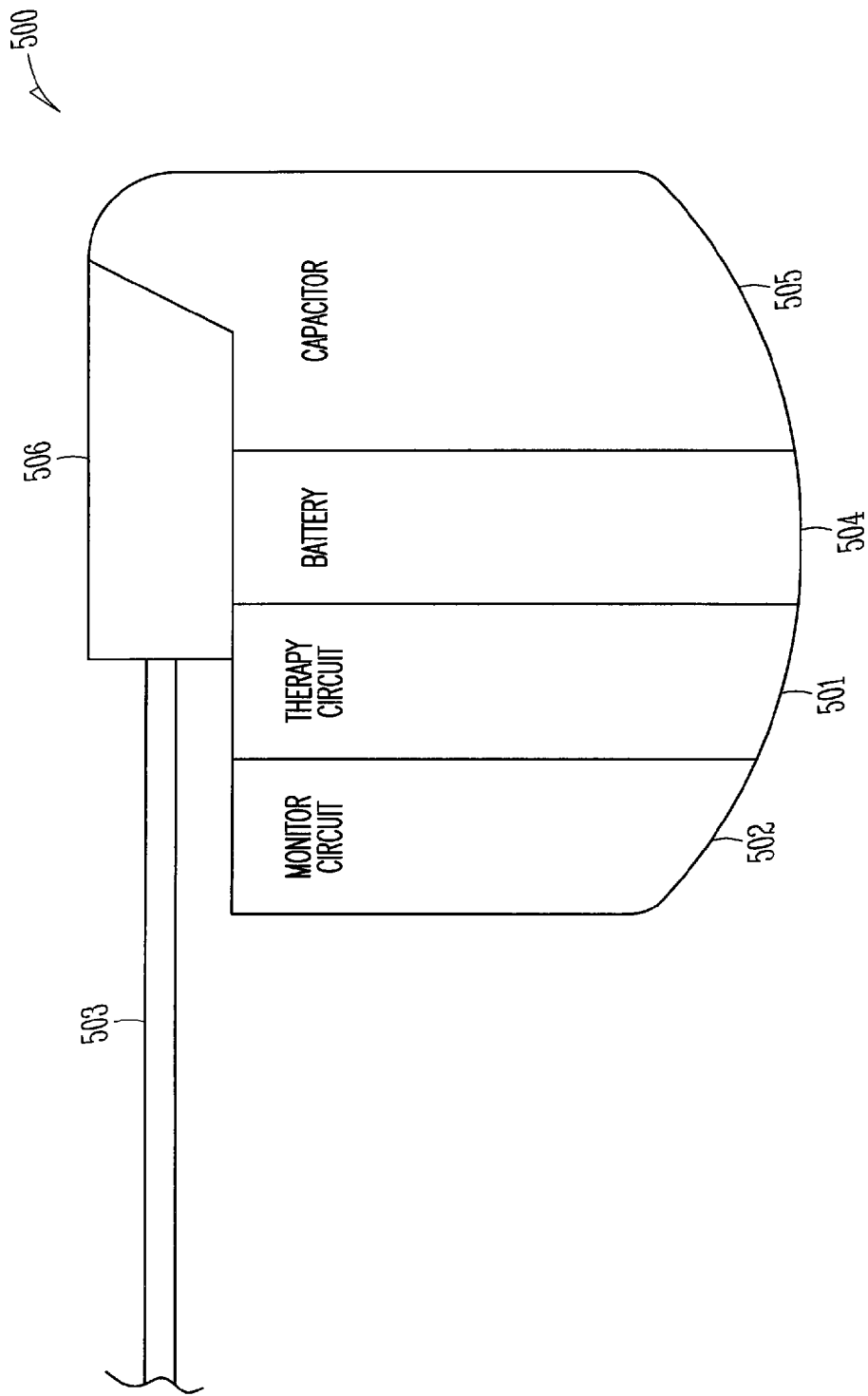
FIG. 5 is a schematic of an implantable device, according to one embodiment of the present subject matter.

FIG. 5 is a schematic of an implantable device, according to one embodiment of the present subject matter. The implantable device 500 is representative of various devices. The present subject matter contemplates any implantable device for providing stimulus, including, but not limited to, pacemakers, defibrillators, cardioverters, congestive heart failure devices, neurostimulation devices and other devices which provide stimulation during implantation.

Implantable device 500 includes a lead system 503. In various embodiments, a lead extends from the device 500 to an area targeted for therapy. In various embodiments, the lead is connected to a feedthrough 506. Various embodiments include a monitoring circuit 502 for monitoring patient activity through one or more of the leads of lead system 503. Various embodiments include a therapy circuit 501 for delivering electrical energy through one or more of the leads. Various embodiments additionally include one or more energy storage components. Some of these embodiments include a battery 504. Various embodiments additionally incorporate at least one capacitor 505. The housing of the present subject matter is used for various components, including, but not limited to, batteries, capacitors, and other components which include a housing.

It should be noted that the side-by-side orientation of the components 502, 501, 504, and 505 of the device 500 is arbitrary, and the illustrated schematic is one embodiment of multiple contemplated by the present subject matter. Additional embodiments include other orientations and configurations not recited herein expressly.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments, and other embodiments will be apparent to those of skill in the art upon reviewing the above description. The scope of the present subject matter should be determined with reference to the appended claims, along with the full scope of equivalents to which such claims are entitled.

We claim:

1. An apparatus, comprising:
a stack of substantially planar electrodes, the stack in alignment and having a stack form factor;
a first planar housing portion including a first beveled edge at least partially defining a first stack aperture adapted to at least partially receive the stack, the first planar housing portion having a first portion having a first thickness proximal the first beveled edge, and a second portion having a second thickness greater than the first thickness, the second portion further away from the first beveled edge than is the first portion; and
a second planar housing portion including a second edge defining a second stack aperture adapted to at least partially receive the stack,
wherein the second planar housing portion is joined to the first planar housing portion such that they are substantially coplanar, wherein the first planar housing portion and the second planar housing portion define an interior space, the first planar housing portion and the second planar housing portion substantially conforming to the stack form factor, with the first portion of the first planar housing spaced orthogonally further from the stack than is the second portion of the first planar housing at a cross section of the first planar housing portion.

2. The apparatus of claim 1, wherein the stack includes a battery stack.

3. The apparatus of claim 1, wherein the stack includes a capacitor stack.

4. The apparatus of claim 1, wherein the joined first and second planar housing portions are smooth along an exterior surface which extends along the first and second thicknesses.

5. The apparatus of claim 1, with the second planar housing portion having a third portion having a third thickness proximal the second edge, and a fourth portion having a fourth thickness greater than the third thickness, the fourth portion further away from the second edge than is the third portion.

6. The apparatus of claim 5, wherein the second planar housing portion defines a second step between the third portion and the fourth portion.

7. The apparatus of claim 6, wherein the first planar housing portion defines a first step between the first portion and the second portion.

8. The apparatus of claim 5, wherein the first thickness is substantially equivalent to the third thickness.

9. The apparatus of claim 8, wherein the second thickness is substantially equivalent to the fourth thickness.

10. The apparatus of claim 1, wherein the first planar housing portion and the second planar housing portion are pressed together.

11. The apparatus of claim 1, wherein the first planar housing portion is cup shaped.

12. The apparatus of claim 11, wherein the second planar housing portion is cup shaped.

13. The apparatus of claim 1, wherein the first planar housing portion and the second planar housing portion encapsulate the stack.

14. The apparatus of claim 1, wherein the first beveled edge and the second edge are in substantially coextensive alignment.

15. The apparatus of claim 14, wherein the second edge is adapted to encourage substantially coextensive alignment of the second edge with the first beveled edge of the first housing portion.

16. The apparatus of claim 1, wherein the first beveled edge of the first housing portion and the second planar housing portion are sealed together with a seal.

17. The apparatus of claim 16, wherein the seal is a hermetic seal.

18. The apparatus of claim 16, wherein the seal includes a weld.

19. The apparatus of claim 1, wherein the second edge includes a bevel.

20. The apparatus of claim 1, wherein the first planar housing portion is part of a drawn housing portion.

* * * * *